(12) United States Patent
Tu et al.

(10) Patent No.: US 6,241,692 B1
(45) Date of Patent: Jun. 5, 2001

(54) ULTRASONIC ABLATION DEVICE AND METHODS FOR LEAD EXTRACTION

(75) Inventors: Hosheng Tu; Cary Hata, both of Tustin, CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 09/167,224

(22) Filed: Oct. 6, 1998

(51) Int. Cl.$^7$ ................................................ A61B 17/22
(52) U.S. Cl. ................... 601/2; 607/116; 606/108
(58) Field of Search .................... 601/2; 600/439; 606/41, 42, 45–52, 108, 1; 607/101, 102, 104, 105, 116

(56) References Cited

U.S. PATENT DOCUMENTS

| | | | |
|---|---|---|---|
| 4,936,281 | * | 6/1990 | Stasz ..................................... 604/222 |
| 5,081,993 | * | 1/1992 | Kitney et al. ........................ 600/454 |
| 5,135,001 | * | 8/1992 | Sinofsky et al. ..................... 600/459 |
| 5,186,177 | * | 2/1993 | O'Donnell et al. .................. 600/462 |
| 5,240,004 | * | 8/1993 | Walinsky et al. ..................... 600/459 |
| 5,779,715 | * | 7/1998 | Tu ........................................... 606/50 |
| 5,855,563 | * | 1/1999 | Kaplan et al. .......................... 604/49 |
| 5,980,515 | * | 11/1999 | Tu .......................................... 606/41 |
| 6,033,402 | * | 3/2000 | Tu et al. ................................ 606/41 |

* cited by examiner

Primary Examiner—Brian L. Casler (57) ABSTRACT

An improved lead extraction system using an ultrasonic transducer with a sharp cutting edge that is useful for the extraction and the removal of unwanted lead by a minimal invasive procedure is described. A lead extraction system suitable for ultrasonic ablation of scar tissues surrounding the implanted lead is comprised of an outer catheter sheath and an inner catheter shaft having a distal end, a proximal end and at least one lumen extending therebetween, wherein an optional locking stylet is provided. In one embodiment, the lead extraction system has a fluid infusion and irrigation means at its distal tip section and an ultrasonic transducer for loosening the target scar tissue by applying ultrasonic energy and cooled fluid to the said transducer and its contacted tissue.

20 Claims, 6 Drawing Sheets

ULTRASONIC ABLATION DEVICE AND METHODS FOR LEAD EXTRACTION

CROSS-REFERENCE TO RELATED APPLICATION

This patent application is related to application "Lead Extraction System and Methods Thereof", Ser. No. 08/880,837, filed Jun. 23, 1997, now U.S. Pat. No. 5,782,900, granted Jul. 21, 1998; and application "Devices and Methods for Lead Extraction", Ser. No. 08/994,550 filed Dec. 19, 1997, now U.S. Pat. No. 5,980,515.

FIELD OF THE INVENTION

The present invention generally relates to the improved system for cardiac lead extraction. More particularly, this invention relates to a catheter system and to methods for removing an implanted endocardial pacemaker lead and/or an implanted transvenous defibrillation lead from the cardiovascular system of a patient using an ultrasonic ablation device.

BACKGROUND OF THE INVENTION

Symptoms of abnormal heart rhythms are generally referred to as cardiac arrhythmias. An abnormally rapid rhythm is referred to as tachycardia, while the arrhythmia rates below the normal rhythm are termed bradycardia. Various factors affect the human heart rate and contribute to the changes of rate from what is termed the normal sinus rate range. These rates generally range in adults from 60 to 100 beats per minute. The heart includes a number of normal pathways, which are responsible for the propagation of electrical signals from the upper to lower chambers, which are necessary for performing normal systole and diastole function.

Treatment of arrhythmias may be accomplished by a variety of approaches, including drugs, surgery, implantable pacemakers/defibrillators, and catheter ablation. While drugs may be the treatment of choice for many patients, they only mask the symptoms and do not cure the underlying causes. Surgical and catheter-based treatments can only cure some simple cases. Implantable devices correct the arrhythmia and prevent it from occurring unexpectedly.

Cardiac pacemakers, chronically implanted within a patient's body, and connected to the heart by at least one lead, are frequently used to control bradycardiac conditions. Recently, implantable cardioverter-defibrillators, also implanted chronically in a patient's body and connected to the heart by at least one lead, can be used to control tachyarrhythmias and life-threatening fibrillations. There are generally two different types of body implantable leads used with cardiac pacemakers: one type, which requires surgery to expose the myocardial tissue, whereby an transducer is affixed to the epicardial tissue; the second type, which can be inserted through a body vessel, such as a vein, into the heart where an transducer contacts the endocardiac tissue. In the second type, the endocardial lead is often secured to the heart through the endocardial lining by a helix, hook, or tines affixed to the distal end of the lead. When the end of the lead contacts the lining of the heart at a desired location, the lead may be secured in place by utilizing lead securing means, such as screwing the helix into the heart tissue, anchoring the hook or engaging the tines.

Similarly, cardioverter defibrillators have used both epicardial leads, that is, leads with transducers attached to the outside of the heart, and endocardial leads, that is, leads inserted into the heart through a body vessel.

With either pacing or defibrillation endocardial leads; fibrotic tissue may eventually encapsulate the leads, especially in areas where there is low velocity blood flow. When small diameter veins, through which the lead passes, become occluded with fibrotic tissue, the separation of the lead from the vein is difficult and can cause severe damage or destruction to the vein. Furthermore, separation may not be possible without constricting the movement of the lead.

In most cases, an endocardial lead will outlast its associated implanted device. However, the lead may become inoperative, or another type of lead may be required. Frequently, the existing lead is left in place, and an additional lead is implanted, rather than risking the removal of the old lead, which was now bonded to the surrounding tissue. Leaving the implanted lead in place, however, particularly in the heart, may further restrict the operation of various heart valves through which the lead passes. If several leads are left in place, operative procedures of the heart and its efficiency may be impaired.

In addition, infection may occasionally develop in or around a lead, requiring surgical removal. In some cases, surgical removal may involve open-heart surgery with its accompanying complications, risks, and costs. These risks are significant for the endocardial pacemaker lead. Because the endocardial defibrillation lead is larger and more complex, the complications associated with the removal of a defibrillation lead can be even greater.

Extraction of chronically implanted leads has been difficult in the past. The problems may include lead fragility and scar tissue encountered along the vein, as well as within the heart. Intravascular countertraction techniques using locking stylets and sheaths via the implant vein, or sheaths, snares, and retrieval baskets via the femoral vein have been described in the literature. Among them, scar tissue was the primary reason for partial or failed removal of a lead. Scar tissue was usually present in multiple locations; the venous entry/subclavian area and the ventricle were the most frequent sites.

Several methods for the removal of pacemaker leads have heretofore been proposed. One method involves a lead removal tool that utilizes a hollow, rigid tube and beveled rod tip for engaging and deforming the coil structure of the heart lead. However, if such a lead can not be removed because of some complication, the tip of the tool is nevertheless locked in place and could not be removed from the lead. Consequently, both the tool and the lead would have to be surgically removed. Moreover, the rigid tube of the tool could easily puncture a blood vessel or a heart cavity wall.

Another method for transvenously extracting a lead involves manual manipulation without the use of an external tool. However, such a method is not possible if the lead has become encapsulated in a blood vessel. Moreover, this method puts excessive strain and tension on the polyurethane or silicone insulation surrounding most pacemaker leads. Should the lead break, the broken inner coil and insulation could damage the heart or the surrounding blood vessels. Surgical removal of the broken lead would be imperative. Moreover, if the pacemaker lead included tines, a corkscrew, or another fixation device at the tip, pulling on the lead could seriously damage the wall of the heart.

Another technique has been proposed in U.S. Pat. No. 4,943,289. This method generally includes the use of a stiffening stylet, which can be inserted into the lead, and then engages the inner coil of the lead near the tip, allowing tension to be applied through the stiffening stylet close to the tip of the lead. This technique also uses pair telescopic flexible tubes that are positioned over the lead to free fiberoptic connections until the tubes are close to the distal tip of the lead. In a related U.S. Pat No. 5,632,749, Goode et al. teaches the use of an anchoring project or expandable means associated with the apparatus for lead extraction.

Another method has been proposed in U.S. Pat. No. 5,620,451. In this patent, Rosborough teaches the use of a flexible coil of flattened ribbon, whereby a cutting surface is provided at the distal end of the coil. It is also discloses that the coil is radiopaque so that its use may be observed in the body by fluoroscopy or other suitable means. Recently, laser ablation devices have been proposed for leads extraction and removal. However, the laser ablation device poses the difficulty for precise controlling the laser energy and avoiding the unwanted vessel perforation.

Of particular interest to the present invention are ultrasonic energy therapeutic protocols, which have been proven to be highly effective in tissue ablation, while exposing a patient to minimal side effects and risks. The traditional radiofrequency ablation provides therapeutic energy by heat conduction while the ultrasonic ablation can provide a deeper energy penetration by remote energy transmissions. By heating the tissues deeply, and causing them to shrink and tighten, the scar tissue bonded to the lead can be loosened and separated from said lead. Ultrasonic energy, when coupled with a temperature control mechanism, can be supplied to the device-to-tissue contact site and deep into the tissue zone precisely to obtain the desired tissue treatment. Ultrasonic energy is conveyed to the tissue by heat conduction and remote penetration.

Marcus et al. in U.S. Pat. No. 5,295,484 and Castellano et al. in U.S. Pat. No. 5,606,974 teach a catheter system having ultrasonic devices for intracardiac ablation of arrhythmias. However, neither patent discloses a medical device having ultrasonic energy therapy in lead extraction processes.

There is therefore a need for a device which comprises a retractable inner catheter having a sharp cutting edge with ultrasonic energy delivery capability, that is useful for extraction and removal of undesired lead by minimally invasive procedures. It would be desirable for such a system to cut through the scars along an implanted lead by utilizing sharp edges of the transducer above-mentioned with assistance of ultrasonic energy for improved lead removal.

SUMMARY OF THE INVENTION

In general, it is an object of the present invention to provide an improved device system for lead removal of either heart pacemaker leads or cardioverter-defibrillator endocardial leads. It is another object of the present invention to provide an improved lead extraction system with an ultrasonic transducer, which can be used in ablating an undesired tissue mass, such as scar tissue or a fibrotic attachment at the venous entry/subclavian area and the ventricle surrounding an implanted lead in a minimally invasive manner.

Also, another object of the present invention is to provide a lead extraction system to irrigate the scar tissue site during the lead extraction. It is still another object of the present invention to provide a method and a device for monitoring the temperature of the medical device, and to control the temperature by utilizing a temperature control mechanism and/or algorithm. The location of the temperature sensor means is preferably at close proximity of the ultrasonic transducer means of the medical device.

In brief, heat is generated by supplying a suitable energy source to a device that is comprised of an energy delivery or electrode means, in contact with the body tissues. A suitable energy source may consist of radiofrequency energy, microwave energy, ultrasonic energy, alternating current energy, or laser energy. The energy can be applied to the scar tissues through the energy delivery or electrode means. A DIP (dispersive indifferent pad) type pad or electrode, which contacts the patient, is connected to the Indifferent Electrode Connector port on an ultrasonic current generator. The generator should usually be grounded to avoid electrical interference. Heat is controlled by the power of the ultrasonic current delivered and by the delivery duration. The standard ultrasonic current generator means, and its applications through an ultrasonic transducer means, to a patient are well known for those who are skilled in the art. More detailed information can be found in U.S. Pat. No. 5,295,484.

The present invention comprises at least one ultrasonic transducer mounted on a distal end portion of a device. The ultrasonic transducer may be a single crystal transducer or a phased array crystal transducer. Ultrasonic transducers adapted for use in the invention are those capable of generating frequencies in the 1–40 MHz range under an applied electrical energy of 1 watt or above. Ultrasonic transducers are typically composed of relatively brittle piezoelectric crystalline material that is somewhat fragile. The ultrasonic transducers may be manufactured in different shape and size. In one embodiment, for energy deep penetration purposes, the ultrasonic transducer has a sharp needle-like end or studded nails to effect the "pressure therapy". The ultrasound transducer further comprises ultrasound crystals adapted to generate at least one of focused ultrasound energy or diffused ultrasound energy.

In one embodiment, a lead extraction system is comprised of an outer catheter sheath and an inner catheter shaft. The catheter sheath is semi-flexible, strong and non-conductive, so that the lead extraction system can follow the implanted lead to its distal end where a scar tissue is attached, and extract said lead out of a patient. The catheter sheath comprises a sheath distal end, a sheath proximal end, and at least one lumen extended therebetween. A handle is secured to the proximal end of the catheter sheath. The catheter sheath contains an ultrasonic transducer at its distal end, whereas the ultrasonic energy is transmitted in the axial direction distal to the distal end. The deployment of the inner catheter shaft is controlled at the proximal end of the handle by a deployment mechanism. The catheter sheath can be advanced along the lead to the scar tissue site to dislodge the lead from said scar tissue by an advancing force at the handle. The transducer deployment means of the catheter sheath includes a retractable tip section that comprises an ultrasonic transducer, having a sharp distal end. In one embodiment, the sharp end has a relatively straight edge. In an alternate embodiment, the sharp end comprises a plurality of sharp points at its edge. In general, the ultrasonic transducer is not conductive. The tip section has a non-deployed state, when the catheter shaft is positioned inside the catheter sheath. This non-deployed state is maintained during the insertion operation of the lead extraction system into a patient, and during withdrawal of the system from the patient. The tip section of the catheter shaft has a deployed state when it is advanced out of the distal end of said catheter sheath. Deployment of the tip section is accomplished by a pushing action on a push-pull or rotating mechanism on the handle. In one embodiment, the degree of deployment is controlled by the pushing action at the push-pull mechanism on the handle and is proportional to the pushing distance on the push-pull plunger, which is quantifiable. The rotation of the catheter sheath can be accomplished either manually, mechanically or electromechanically from a rotating means located at the proximal end of the handle.

The distal end of the deployed ultrasonic transducer defines an ablation target of the scar tissue covering the implanted lead. The sharp distal end of the transducer is positioned to directly face the target scar tissue. A conducting wire which is secured to the base of the ultrasonic transducer means, passes through the lumen of the catheter sheath and through the interior void of the handle, and is thereafter secured to a contact pin of the connector at the proximal end of the handle. Therefrom, the conducting wire is connected to an external ultrasonic current generator for ultrasonic energy delivery.

During lead extraction operations, the lead extraction system, comprised of an outer catheter sheath and an inner catheter shaft, is inserted into the body through a natural body opening by sliding over an existing lead. After the system approaches the target scar tissue mass to be treated, the tip section of the catheter shaft is deployed by being pushed out of the catheter sheath from a deployment mechanism at the handle. Once positioned, the sharp ends of the ultrasonic transducer encircle the tissue mass. By a simultaneous or alternate mode, gradually pushing forward the catheter shaft against the tissue mass, and applying ultrasonic energy, the target tissue mass is loosened as a result of a combination of the ultrasonic energy, and mechanical cutting forces of the sharp ends of the ultrasonic transducer.

A fluid source is positioned at the proximal end of the handle for supplying a fluid flow through a lumen of said catheter sheath or shaft to the tip section, which contains a fluid vent opening. Therefore, at ablation time, the tip section with the ultrasonic transducer is positioned against the tissues to be ablated. The fluid is continuously or intermittently supplied through the opening to cover and rinse the tissue contact site of the transducers to render therapeutic purposes. The appropriate fluid flow rate for fluid irrigation is preferably in the range of 5 cc/min to 20 cc/min. Therapeutic fluid can also be supplied through the existing fluid by conveying/irrigation means.

A fluid conveying lumen is associated with the elongated catheter sheath or catheter shaft, and is preferably disposed of within a separate lumen of the catheter shaft along the longitudinal axis thereof. The lumen is adapted to communicate with the fluid-supplying source, to convey fluid from the source and through the lumen to be discharged through the vent opening of the tip section and diffused out of the tip section containing the ultrasonic transducer.

This invention also comprises optionally a method and a system for controlling the flow rate of fluid through the lumen to optimize the energy delivering transducer means of the lead extraction system. The control system preferably regulates the flow rate based on signals representative of the temperature of the transducer tip and/or tissue impedance.

In a further embodiment, after the lead and its surrounding tissue is loosened, a locking stylet is used to engage the lead with the lead extraction system and the lead is removed by the said lead extraction system thereafter.

The system and methods of the present invention have several significant advantages over the currently known lead extraction systems or methods. In particular, the ultrasonic transducer having ultrasound ablation capabilities of this invention results in a more effective means for cutting loose the scar tissue and has a more effective means for removing the undesired lead from the implanted site.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
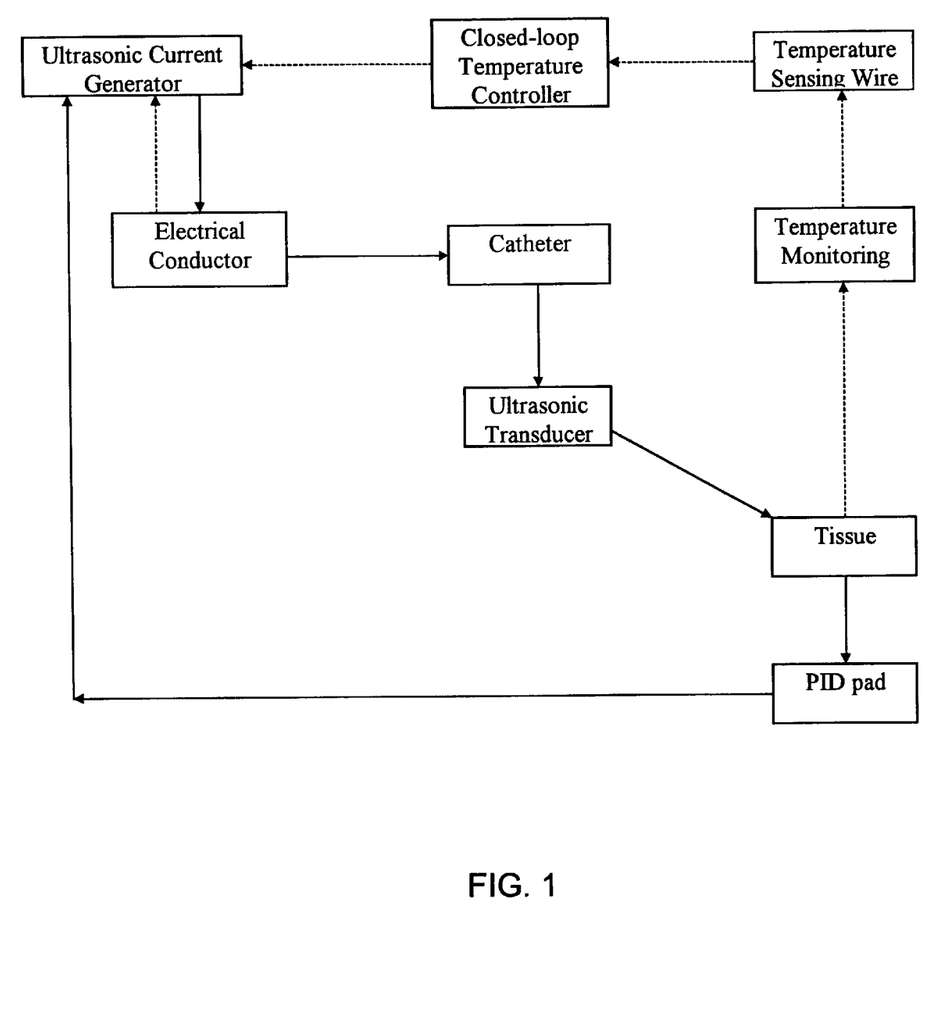
FIG. 1 is a schematic diagram of the ultrasonic transducer principles for the lead extraction procedures in a patient.

What is shown in FIG. 1 to FIG. 6 is a lead extraction system constructed in accordance with the principles of the present invention comprising an outer catheter sheath and an inner catheter shaft. FIG. 1 shows a schematic diagram of the principles of the ultrasonic ablation in a patient. A DIP (dispersive indifferent pad) type pad, which contacts the patient, is connected to the Indifferent Electrode Connector port on an ultrasonic current generator. A catheter with an ultrasonic transducer is connected to the generator. The generator should usually be grounded to avoid electrical interference. The ultrasonic current is delivered through an electrical conductor to the transducer of a catheter. The ultrasonic energy is thereafter delivered to the tissue through the tissue contact. Heat is controlled by the power of the ultrasonic current delivered and by the delivery duration.

Figure 2:
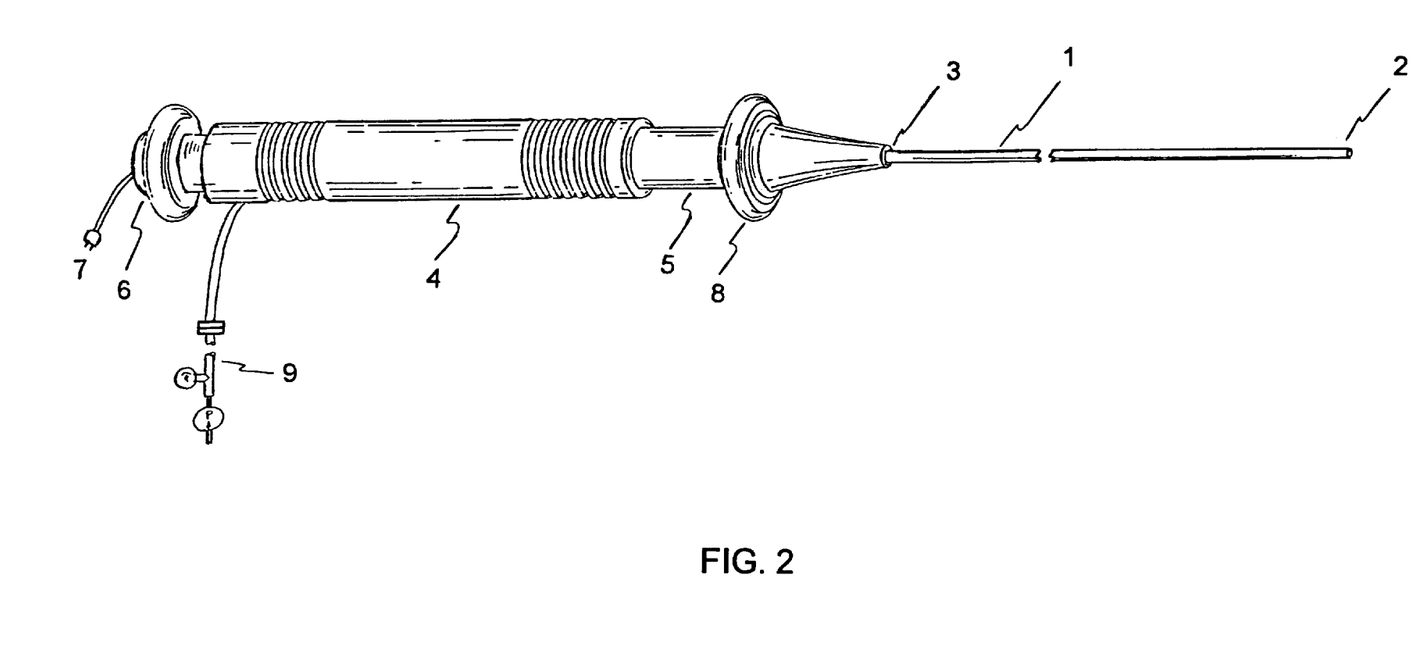
FIG. 2 is an overall view of the lead extraction system containing an ultrasonic transducer means at its distal tip section constructed in accordance with the principles of the present invention.

FIG. 2 shows an overall view of the lead extraction system having a catheter sheath 1. The catheter sheath has a sheath distal end 2, a sheath proximal end 3, and at least one lumen 41 extending between the sheath distal end 2 and the sheath proximal end 3, wherein there is at least one opening at the sheath distal end 2. A handle 4 is attached to the proximal end 3 of the catheter sheath 1, wherein the handle has a cavity. A catheter shaft 10 is located inside the catheter sheath 1, the catheter shaft 10 having a shaft distal tip section, a shaft distal end 18, a shaft proximal end and at least one lumen 42 extending between the shaft distal end 18 and shaft proximal end. At least one ultrasonic transducer 20 is disposed at the shaft distal end 18 of said catheter shaft 10, the ultrasonic transducer 20 has a transducer distal end 19 and transducer proximal end 25. There is at least one opening at the transducer distal end 19. A deployment means 5 is mounted on the handle 4 for the shaft distal tip section of said catheter shaft 10, wherein the deployment means 5 has a deployed state and a non-deployed state for the catheter shaft 10. The proximal end of said catheter shaft 10 is secured to the deployment means 5. In one alternate embodiment, the deployment means 5 is a push-pull type mechanism 8. A connector means 7 for a conducting wire 31 is used to transmit the ultrasonic current and is located at the very proximal end 6 of the handle 4. In one optional embodiment, a fluid irrigation means 9 is located close to the proximal end of the handle 4, wherein the fluid irrigation means has an opening 43 at the transducer distal end 19.

Figure 3:
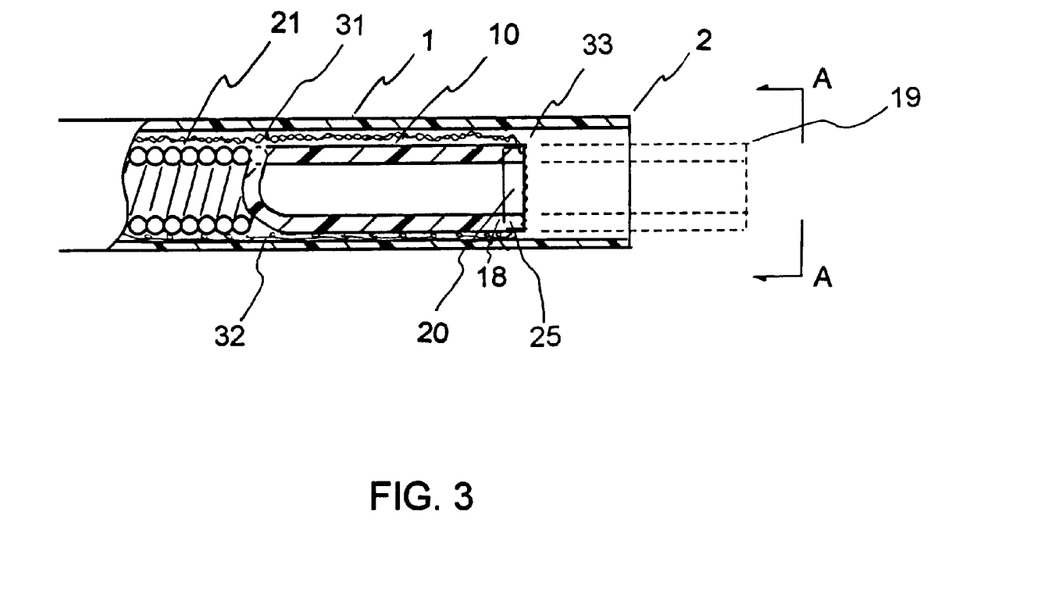
FIG. 3 is a cross-sectional view of the distal section of the lead extraction system of the present invention.

FIG. 3 shows a cross-sectional view of the distal tip section of the lead extraction system, which is comprised of an outer catheter sheath 1 and an inner catheter shaft 10. The catheter shaft 10 can be deployed longitudinally, relative to the catheter sheath 1.

Figure 4:
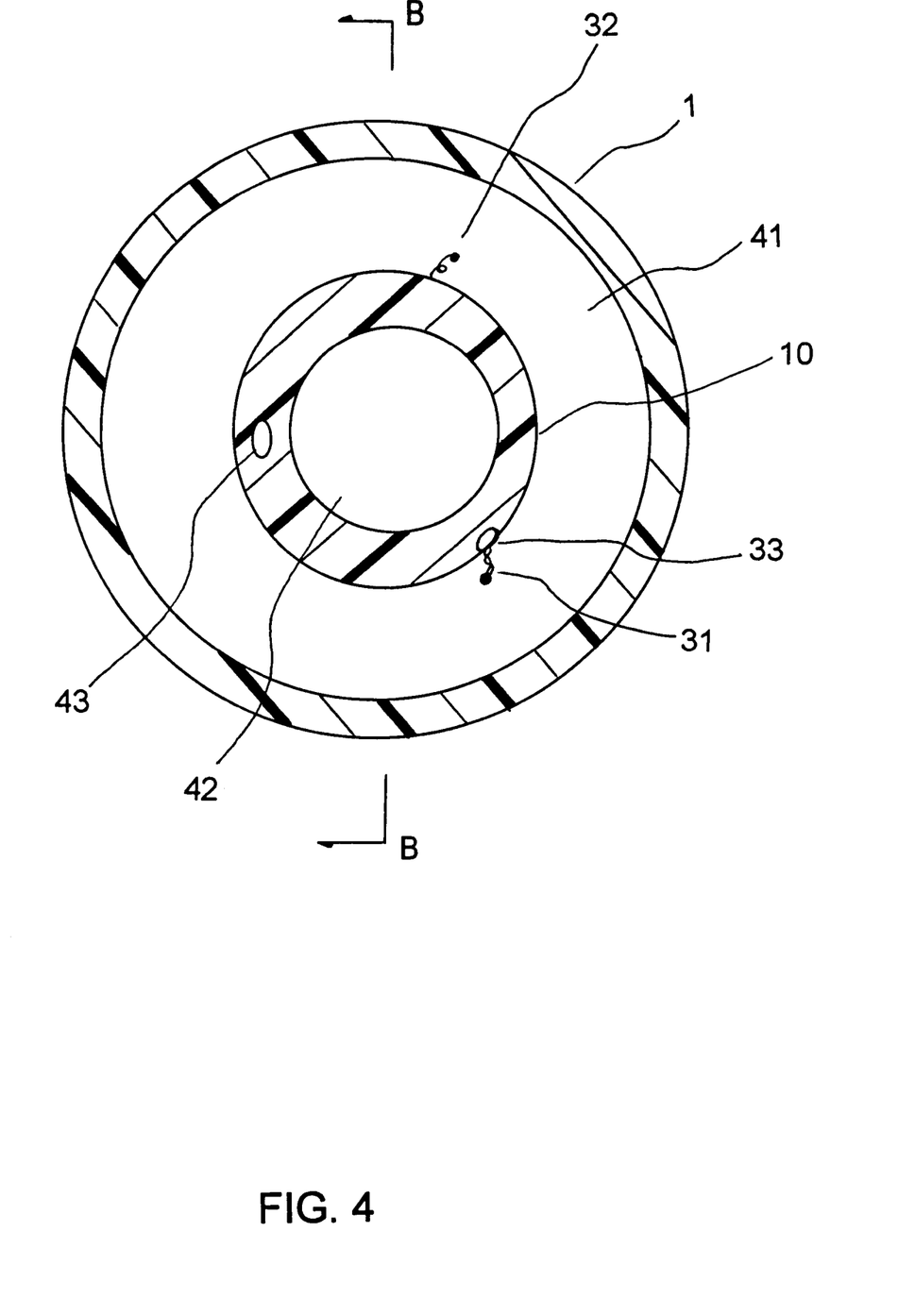
FIG. 4 is a side view of the A—A section of FIG. 3, showing the distal end of the lead extraction system.

FIG. 4 is a side view of the A—A section of FIG. 3, which shows the distal end 2 of the lead extraction system. A catheter shaft 10 is located within the lumen 41 of the catheter sheath 1. The lumen 42 of the inner catheter shaft 10 is to ride on the implanted lead so that the lead extraction system can advance to the tissue site 24. An insulated conducting wire 32 for ultrasonic current transmission and a temperature sensing wire 31 are located within the lumen of the catheter sheath 41.

Figure 5:
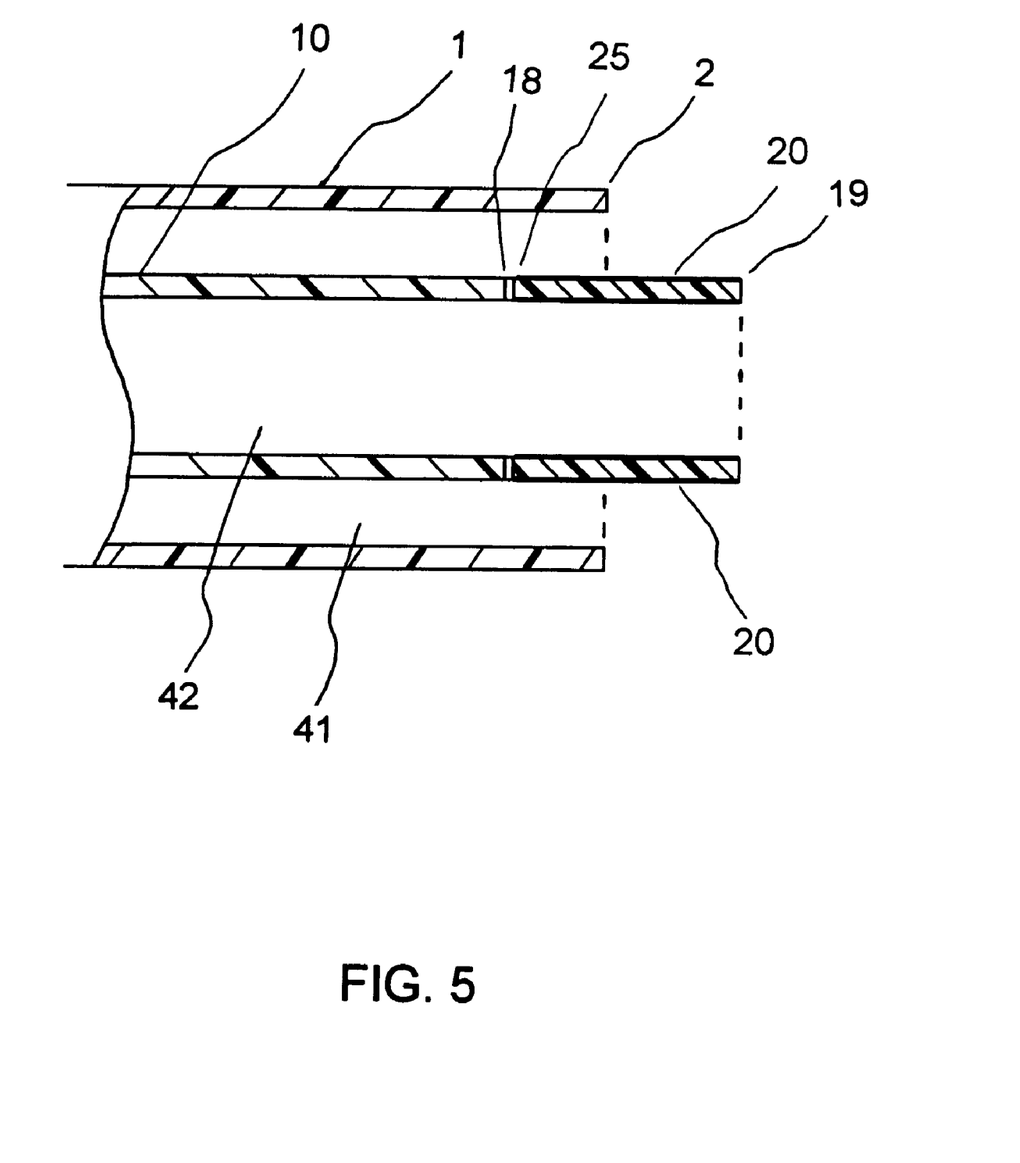
FIG. 5 is a side view of the B—B section of FIG. 4, showing the distal tip portion of the ultrasonic transducer, the outer catheter sheath and the inner catheter shaft.

FIG. 5 is a side view of the B—B section of FIG. 4, which shows the outer catheter sheath 1, the inner catheter shaft 10, and the ultrasonic transducer 20. The ultrasonic transducer 20 is mounted at the shaft distal end 18 and has a transducer distal end 19 and a transducer proximal end 25. The transducer 20 can be deployed out of the sheath distal end 2 of the catheter sheath 1. Under a non-deployed state, the catheter shaft 10 is located within the lumen of the catheter sheath 1. Upon transducer deployment, the distal tip section of the catheter shaft 10 is pushed out of the tip 2 of the catheter sheath 1. To improve its flexibility and torqueability, a portion of the catheter shaft 10 may be made of a coil or meshed wire, which can also serve as the transmission means for ultrasonic current delivery to the transducer 20.

In a further embodiment, the lead extraction system may further comprise a stylet locking mechanism at the handle 4 for controlling the advancement and locking activities of the locking stylet of the catheter shaft 10. A stylet-locking plunger of the locking mechanism at the handle is used to control the degree of the advancement of the locking stylet of the catheter sheath. The stylet locking mechanism on the lead extraction system is well known to those who are skilled in the art.

In an additional embodiment, the lead extraction system further comprises a temperature sensing and closed-loop temperature control mechanism for the ultrasonic transducer having a temperature sensor 33 near the tissue contact site. Temperature sensing wires 31 along with a thermocouple or thermistor means is provided to transmit the temperature data from the tissue contact site to an external temperature measuring and control apparatus. An algorithm is equipped for the ablation system so that a closed-loop temperature control is effective and the temperature data is relayed to an external ultrasonic generator (not shown) for controlled current delivery.

The external ultrasonic energy generator means has the capability to supply ultrasonic energy by controlling the time, power, and temperature through an optionally separate closed-loop temperature control means. The patient is connected to the ultrasonic energy generator means through a DIP electrode to form a closed-loop current system. Therefore, ultrasonic energy is applied and delivered to the targeted scar tissue, through the ultrasonic transducers of this invention. The ultrasonic energy current in this invention is preferably within the range of 1 to 40 MHz. The electricity comprises applying at least 1 watt to the ultrasonic transducer. One material used to make piezoelectric transducers is barium titanate. The barium titanate has high sensitivity as an ultrasonic transducer, which means that it requires small voltage amplification. Barium titanate is also substantially more durable under mechanical and environmental abuse than other piezoelectric crystals and can sustain its property at a relatively high temperature.

In an additional embodiment, the lead extraction system comprises a fluid supplied to the shaft distal end 19 of the catheter shaft 10 and is diffused out of the shaft distal end of said catheter shaft. The fluid may be selected from the group consisting of saline, heparin, antibiotics, anti-inflammatory, chemotherapy, and therapeutics fluids.

Figure 6:
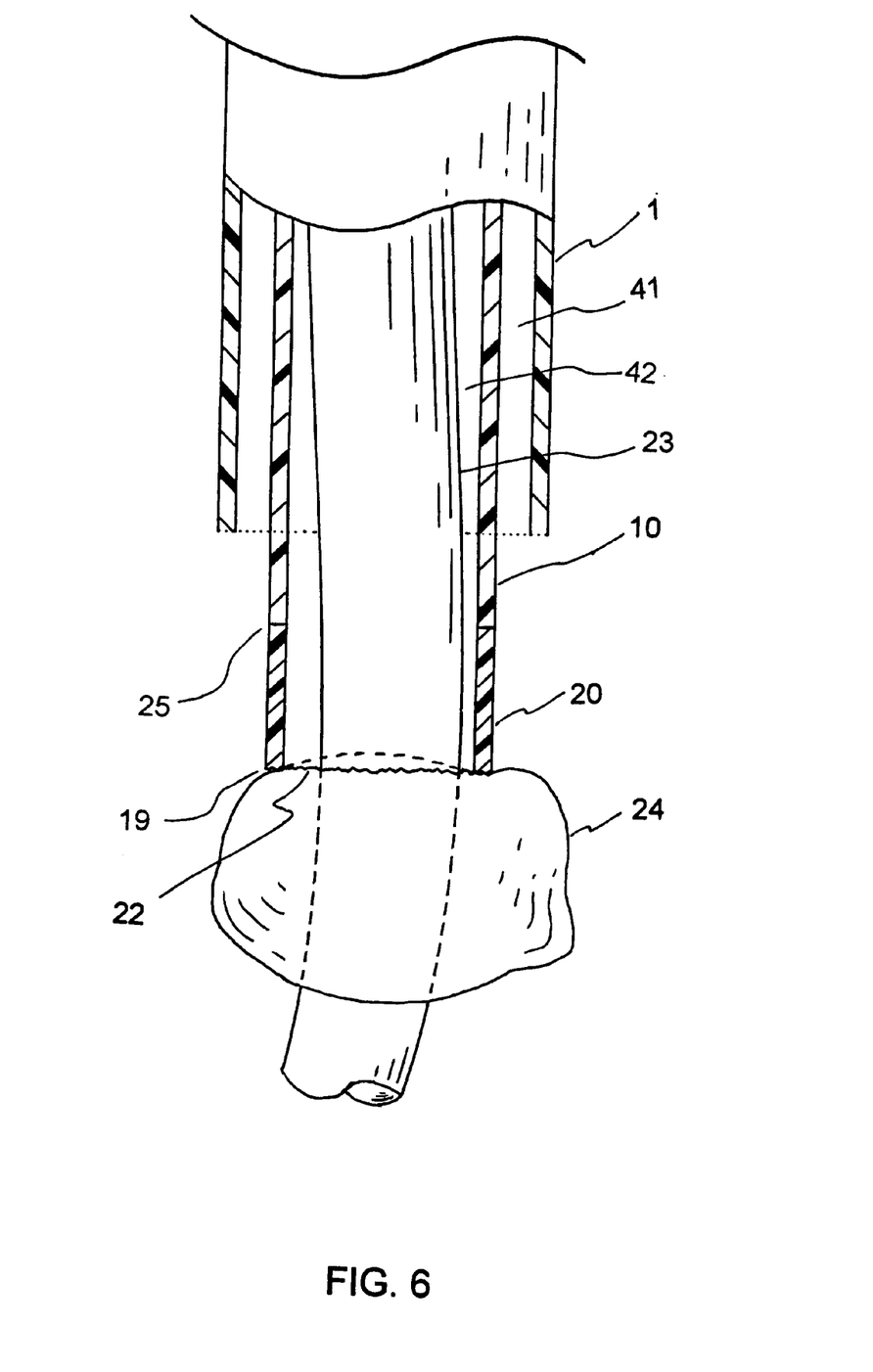
FIG. 6 is a simulated lead extraction operation of the lead extraction system on an implanted lead.

FIG. 6 is a close-up view of the lead extraction operation of the lead extraction system. An implanted lead 23 with its surrounding scar tissue 24 is to be removed from the body of a patient. The ultrasonic transducer 20 is positioned to have its sharp edge 19 contacting the scar tissue 24. The catheter shaft 10 is located within the lumen 41 of the catheter sheath 1 at a non-deployed state. By way of illustration, a lead extraction system of this invention is inserted along or is slid over the existing lead wire through a vein. The system is positioned near the target tissue site where the catheter sheath contacts the tissue. The catheter shaft is deployed and the sharp edge of the transducer firmly contacts the tissue to be ablated. The sharp edge 19 of the ultrasonic transducer 20 is used to cut through the scar tissue associated with the implanted lead. By a combination of the following actions: gradually pushing forward the catheter shaft against the tissue mass, rotating the ultrasonic transducer, and applying ultrasonic energy to the ultrasonic transducer, the target tissue mass is loosened and separated from the lead. Thereafter, the lead can then be removed with ease.

A method for operating a lead extraction system for removing a lead out of a patient is illustrated. The lead extraction system comprises an outer catheter sheath, an inner catheter shaft having a shaft distal end, and a shaft deployment means. An ultrasonic transducer is mounted at the distal end of said catheter shaft, wherein it is connected to an ultrasonic current generator. The method comprises the steps of: (a) sliding the lead extraction system over an existing lead in a patient, wherein said lead is surrounded by a scar tissue; (b) intimately contacting the shaft distal end of the catheter shaft with the scar tissue; (c) deploying the catheter shaft containing an ultrasonic transducer at its distal end; (d) applying an ultrasonic current from the ultrasonic current generator to the ultrasonic transducer; and (e) extracting the lead by pulling the lead extraction system out of a patient.

In an alternate mode, a method for operating a lead extraction system for removing a lead out of a patient is illustrated. The lead extraction system comprises a catheter sheath having a sheath distal end, a sheath proximal end, and at least one lumen extending between the sheath distal end and sheath proximal end, wherein there is at least one opening at the sheath distal end. A handle is attached to the sheath proximal end of the catheter sheath, wherein the handle has a cavity. A catheter shaft is located inside the catheter sheath, the catheter shaft having a shaft distal tip section, a shaft distal end, a shaft proximal and at least one lumen extending between the shaft distal end and shaft proximal end. At least one ultrasonic transducer is disposed at the shaft distal end of said catheter shaft, wherein there is at least one opening at the shaft distal end. The system has a deployment means for the shaft distal tip section of said catheter shaft, wherein the deployment means has a deployed state and a non-deployed state for the catheter shaft, and wherein the proximal end of said catheter shaft is secured to the deployment means. The transducer is connected to an ultrasonic current generator. The method comprises the steps of: (a) sliding the lead extraction system over an existing lead in a patient, wherein said lead is surrounded by a scar tissue; (b) intimately contacting the shaft distal end of the catheter shaft with the scar tissue; (c) deploying the catheter shaft containing an ultrasonic transducer at its distal end; (d) applying an ultrasonic current to the ultrasonic transducer; and (e) extracting the lead by pulling the lead extraction system out of a patient.

From the foregoing, it should now be apparent that an improved lead extraction system comprised of an ultrasonic transducer with ultrasonic energy delivery capability has been disclosed for removing the implanted lead from a patient. While this invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A lead extraction system comprising:
a catheter sheath having a sheath distal end, a sheath proximal end, and at least one lumen extending between the sheath distal end and sheath proximal end, wherein there is at least one opening at the sheath distal end;
a handle attached to the sheath proximal end, wherein the handle has a cavity;
a catheter shaft located inside the catheter sheath, the catheter shaft having a shaft distal tip section, a shaft distal end, a shaft proximal and at least one lumen extending between the shaft distal end and shaft proximal end, wherein at least one ultrasonic transducer is disposed at the shaft distal end of said catheter shaft, the transducer having a transducer proximal end and a transducer proximal end, wherein there is at least one opening at the transducer distal end; and
a deployment means for the shaft distal tip section of said catheter shaft, wherein the deployment means has a deployed state and a non-deployed state for the catheter shaft, and wherein the proximal end of said catheter shaft is secured to the deployment means.

2. The lead extraction system as in claim 1 further comprising an ultrasonic current generator, wherein an ultrasonic current is delivered to the at least one ultrasonic transducer.

3. The lead extraction system of claim 2, wherein the at least one ultrasonic transducer has a distal sharp-edge.

4. The lead extraction system of claim 2, wherein the ultrasonic current is adapted to said at least one ultrasonic transducer sufficient to cause the ultrasonic transducer to resonate with frequency of about 1 to 40 MHz.

5. The lead extraction system as in claim 2 further comprising at least one temperature sensing means and a closed-loop temperature control means for the lead extraction system, wherein a temperature sensed from the at least one temperature sensing means is relayed to the closed-loop temperature control means for controlling an ultrasonic current delivery.

6. The lead extraction system as in claim 1 further comprising a locking stylet located within the lumen of said catheter sheath.

7. The lead extraction system as in claim 1 further comprising a fluid supplied to the shaft distal end of the catheter shaft and is diffused out of the shaft distal end of said catheter shaft.

8. The lead extraction system of claim 7, wherein the fluid is selected from the group consisting of saline, heparin, antibiotics, anti-inflammatory, chemotherapy and therapeutics fluids.

9. The lead extraction system as in claim 4 further comprising means for controlling the flow rate of the fluid through the lumen of the catheter shaft.

10. The lead extraction system of claim 1, wherein the at least one ultrasound transducer further comprises ultrasound crystals adapted to generate at least one of focused ultrasound energy or diffused ultrasound energy.

11. A method for operating a lead extraction system for removing a lead out of a patient, the lead extraction system comprising an outer catheter sheath, an inner catheter shaft having a shaft distal end and a shaft deployment means, an ultrasonic transducer mounted at the distal end of said catheter shaft, and an ultrasonic current generator; the method comprising the steps of:
(a) sliding the lead extraction system over an existing lead in a patient, wherein said lead is surrounded by a scar tissue;
(b) intimately contacting the shaft distal end of the catheter shaft with the scar tissue;
(c) deploying the catheter shaft containing an ultrasonic transducer at its distal end;
(d) applying an ultrasonic current from the ultrasonic current generator to the ultrasonic transducer; and
(e) extracting the lead by pulling the lead extraction system out of a patient.

12. The method for operating the lead extraction system as in claim 11 further comprising supplying a fluid to the ultrasonic transducer of the catheter shaft.

13. The method for operating the lead extraction system as in claim 11 further comprising at least one temperature sensing means and a closed-loop temperature control means for the lead extraction system, wherein a temperature sensed from the at least one temperature sensing means is relayed to the closed-loop temperature control means for controlling an ultrasonic current delivery.

14. The method for operating the lead extraction system of claim 11, wherein the ultrasonic current is adapted to said ultrasonic transducer sufficient to cause the ultrasonic transducer to resonate with frequency of about 1 to 40 MHz.

15. The method for operating the lead extraction system of claim 11, wherein the ultrasound transducer further comprises ultrasound crystals adapted to generate at least one of focused ultrasound energy or diffused ultrasound energy.

16. A method for operating a lead extraction system for removing a lead out of a patient, the lead extraction system comprising a catheter sheath having a sheath distal end, a sheath proximal end, and at least one lumen extending between the sheath distal end and sheath proximal end, wherein there is at least one opening at the sheath distal end; a handle attached to the proximal end of the catheter sheath, wherein the handle has a cavity; a catheter shaft located inside the catheter sheath, the catheter shaft having a shaft distal tip section, a shaft distal end, a shaft proximal end and at least one lumen extending between the shaft distal end and shaft proximal end, wherein at least one ultrasonic transducer is disposed at the shaft distal end of said catheter shaft, and wherein there is at least one opening at the shaft distal end; and a deployment means for the shaft distal tip section of said catheter shaft, wherein the deployment means has a deployed state and a non-deployed state for the catheter shaft, and wherein the proximal end of said catheter shaft is secured to the deployment means, and an ultrasonic current generator;

the method comprising the steps of:
(a) sliding the lead extraction system over an existing lead in a patient, wherein said lead is surrounded by a scar tissue;
(b) intimately contacting the shaft distal end of the catheter shaft with the scar tissue;
(c) deploying the catheter shaft containing an ultrasonic transducer at its distal end;

(d) applying an ultrasonic current to the ultrasonic transducer; and (e) extracting the lead by pulling the lead extraction system out of a patient.

17. The method for operating the lead extraction system as in claim 16 further comprising supplying a fluid to the ultrasonic transducer of the catheter shaft.

18. The method for operating the lead extraction system as in claim 16 further comprising at least one temperature sensing means and a closed-loop temperature control means for the lead extraction system, wherein a temperature sensed from the at least one temperature sensing means is relayed to the closed-loop temperature control means for controlling an ultrasonic current delivery.

19. The method for operating the lead extraction system of claim 16, wherein the ultrasonic current is adapted to said ultrasonic transducer sufficient to cause the ultrasonic transducer to resonate with frequency of about 1 to 40 MHz.

20. The method for operating the lead extraction system of claim 16, wherein the ultrasound transducer further comprises ultrasound crystals adapted to generate at least one of focused ultrasound energy or diffused ultrasound energy.

* * * * *